(12) United States Patent
Lok

(10) Patent No.: US 6,908,751 B2
(45) Date of Patent: Jun. 21, 2005

(54) METHODS FOR ENHANCING THE EXPRESSION OF A PROTEIN OF INTEREST BY RECOMBINANT HOST CELLS

(75) Inventor: Si Lok, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 341 days.

(21) Appl. No.: 09/842,746

(22) Filed: Apr. 25, 2001

(65) Prior Publication Data

US 2002/0019049 A1 Feb. 14, 2002

Related U.S. Application Data

(60) Provisional application No. 60/199,760, filed on Apr. 26, 2000.

(51) Int. Cl.[7] .......................... C12P 19/32; C12P 19/34; C12N 15/64; C12N 15/66
(52) U.S. Cl. .................. 435/91.52; 435/91.1; 435/91.4; 435/91.41

(58) Field of Search .............................. 435/91.1, 91.4, 435/91.41, 91.52

(56) References Cited

U.S. PATENT DOCUMENTS 6,495,318 B2 * 12/2002 Harney .......................... 435/6

* cited by examiner

*Primary Examiner*—James Ketter
*Assistant Examiner*—Konstantina Katcheves
(74) *Attorney, Agent, or Firm*—Michelle L. Johnson; Phillip B.C. Jones

(57) ABSTRACT

The increased use of nucleotide sequence data mining techniques has amplified the demand for efficient methods of producing recombinant proteins in eukaryotic cells. A strategy is provided for enhancing the synthesis of recombinant amino acid sequences by polymerizing expression cassettes in vitro before producing recombinant hosts.

13 Claims, No Drawings

METHODS FOR ENHANCING THE EXPRESSION OF A PROTEIN OF INTEREST BY RECOMBINANT HOST CELLS

CROSS-REFERENCE TO RELATED APPLICATIONS

This application claims the benefit of U.S. Provisional application No. 60/199,760 (filed Apr. 26, 2000), the contents of which are incorporated by reference.

TECHNICAL FIELD

The present invention relates generally to methods for increasing the production of a desired protein by recombinant host cells. In particular, the present invention relates to a novel strategy for producing eukaryotic host cells with genes polymerized in vitro.

BACKGROUND OF THE INVENTION

The increased use of nucleotide sequence data mining techniques has highlighted the need for efficient methods of producing recombinant proteins. While it is possible to use bacteria to synthesize recombinant protein, this approach cannot be conveniently applied to eukaryotic proteins that require post-translational modification for their activity. Moreover, foreign proteins may be recognized as such by bacterial host specific proteases, resulting in a low protein yield.

One strategy for obtaining a high yield of a recombinant protein by eukaryotic cells is to increase the gene dosage. This can be achieved with viral vectors, such as bovine papilloma virus, simian virus 40, and Epstein-Barr virus, which provide a high copy number per cell (see, for example, DiMaio et al., Proc. Nat'l Acad. Sci. USA 79:4030 (1982); Yates et al., Nature 313:812 (1985)). However, the use of these episomal systems is limited to certain permissive host cells that can support viral replication. In addition, expression is often transient due to vector instability.

Vector stability is improved when the vector is integrated into the genomic DNA of the host cell. Another approach, therefore, is to select cells containing vector sequences, which have been amplified after integration into genomic DNA. Typically, the selection procedure is performed by transfecting cells with a gene encoding the desired protein and a gene that encodes a protein, which confers resistance to a toxic drug. The co-amplification of transfected DNA can provide a 100- to 1000-fold increase in the expression of the desired protein.

Although over twenty selectable and amplifiable genes have been described, the most popular selectable marker gene for amplification is the dihydrofolate reductase (DHFR) gene (Kaufman, Methods Enzymol. 185:487 (1990)). In this approach, the copy numbers of the DHFR gene and an associated gene are increased by selection in methotrexate, which is a competitive inhibitor of the DHFR enzyme. Stepwise increases in methotrexate concentration result in the selection of clones that often express elevated levels of DHFR, usually due to gene amplification, and increased expression of the co-amplified gene. One disadvantage of DHFR co-amplification is the requirement of a DHFR-deficient cell line. Another drawback is that the methotrexate dose must be increased in small increments in a stepwise amplification with clones picked and expanded at each step. Consequently, a significant investment in time is required to obtain a highly amplified clone (see, for example, Barsoum, DNA and Cell Biology 9:293 (1990)). As an illustration, Chinese hamster DHFR$^-$ cells are often used for the synthesis of recombinant proteins because the recombinant genes integrated into the host chromosome along with the DHFR gene can be efficiently co-amplified by increasing the methotrexate concentration. However, it normally takes six to ten months to establish cell lines that produce desired amounts of recombinant proteins after transfection (see, for example, Choo et al., Gene 46:277 (1986)).

Gene amplification has also been obtained using selectable marker genes such as adenosine deaminase genes, ornithine decarboxylase genes, and the human multidrug resistance gene, MDR1 (Kaufman et al., Proc. Nat'l Acad. Sci. USA 83:3136 (1982); Chiang and McConlogue, Mol. Cell. Biol. 8:764 (1988); Germann et al., J. Biol. Chem. 264:7418 (1989); Kane et al., Mol. Cell. Biol. 8:3316 (1988)). Kaufman, U.S. Pat. No. 5,238,820, took advantage of the availability of multiple amplifiable genes by designing vectors that carry two or more different heterologous selectable amplifiable marker genes. The objective was to achieve higher levels of gene amplification. In this approach, transformed cells are first grown under suitable conditions for selecting and amplifying one heterologous selectable amplifiable marker gene to increase the copy number of the desired protein gene. The copy number is then further increased by growing the cells under suitable conditions for selecting, and amplifying the second heterologous selectable amplifiable marker gene. This process is repeated for each additional selectable marker that may be present.

Studies indicate that, when plasmids reach a host cell nucleus, the plasmids are cleaved and spliced into high molecular weight concatemers. In vivo gene amplification has the disadvantage that the structure of the amplified gene cannot be controlled, and success is not predictable. Barsoum, DNA and Cell Biology 9:293 (1990), described a high copy number electroporation of Chinese hamster ovary cells with high concentrations of expression vector, which had been linearized with a restriction endonuclease that left cohesive ends. A significant portion of the introduced DNA was arranged in tandem repeats of unknown length that comprised the copies of the vector in mixed orientations. Although this method provided control over the plasmid cleavage site, in vivo ligation and integration events were not controlled.

One strategy for imposing greater control into the gene amplification process is to polymerize the gene of interest in vitro before introducing the DNA into a host cell (see, for example, Leahy et al., Bioconjugate Chem. 7:545 (1996); Leahy et al., Nucl. Acids Res. 25:449 (1997)). Early attempts to generate tandem arrays of DNA fragments required the ligation of the DNA fragment into an appropriate vector, and typically, this simple approach yielded a random orientation of fragments, resulting in polymers containing both direct and inverted repeats (see, for example, Sadler et al., Gene 3:211 (1978)). While the presence of inverted repeats in a polymer led to instability of the DNA inside the host cell, a series of direct repeats was found to form stable molecules.

A problem in controlling fragment orientation is that many of the commonly used restriction enzymes produce termini that are rotationally equivalent, and therefore, self-ligation of DNA fragments with such termini is random with regard to fragment orientation. Hartley and Gregori, Gene 13:347 (1981), reported a technique to control fragment orientation during ligation, which required the introduction of AvaI sites flanking either end of the cloned fragment (also see Hartley and Gregori, U.S. Pat. No. 4,403,036). Since AvaI cleavage produces distinguishable ends, self-ligation of the fragment results in a strong bias toward head-to-tail orientation. This is so because head-to-head and tail-to-tail ligation results in base mismatches. The polymerized molecules were then inserted into a vector and used to transform E. coli.

In a similar approach, Ikeda et al., Gene 71:19 (1988), produced head-to-tail tandem arrays of a DNA fragment encoding a human major histocompatibility antigen that was flanked by SfiI cleavage sites. SfiI produces cleaved ends that are not rotationally equivalent. A cosmid vector containing the amplified gene and hygromycin B resistance-conferring and dhfr genes was used to transfect a murine cell line.

SfiI sites have also been used to produce copolymers of gene expression cassettes and selection markers, which can be used to transfect cells (Monaco et al., Biotechnol. Appl. Biochem. 20:157 (1994); Asselbergs et al., Anal. Biochem. 243:285 (1996)). According to the method of Monaco et al., the copolymer is treated with NotI to cleave the DNA at the 3'-end of the selectable marker gene. In this way, transfected DNA molecules will contain only one selectable marker gene per copolymer.

Class IIS restriction enzymes can generate totally asymmetric site and complementary cohesive ends. Kim and Szybalski, Gene 71:1 (1988), took advantage of this quality by introducing sites for BspMI, a class-IIS restriction enzyme, at either end of cloned DNA. Self-ligation of the cloned DNA provided multimers comprising repeat units in the same orientation. Similarly, Takeshita et al., Gene 71:9 (1988), achieved tandem gene amplification by inserting a fragment encoding human protein C into a plasmid to introduce asymmetric cohesive ends into the fragment. In this case, sites for the class IIS enzyme, BstXI, were used. The multimer was then cloned into a cosmid vector comprising a neo gene, packaged into lambda phage particles, and amplified in E. coli. The cosmid vectors were then introduced into Chinese hamster ovary DHFR-cells, which were treated with G418 to select for cells that expressed the neo gene. Takeshita et al. also found that cells expressed human protein C, albeit at lower levels, following transfection with unpackaged tandem ligated DNA comprising copies of the cosmid vector and the human protein C gene.

A similar approach was also described by Lee et al., Genetic Analysis: Biomolecular Engineering 13:139 (1996), who amplified target DNA as tandem multimers by cloning the target DNA into a class IIS restriction enzyme cleavage site of a vector, excising a monomeric insert with the class IIS restriction enzyme, isolating monomeric inserts, self-ligating the inserts, and cloning the multimers into a vector. According to Lee et al., this scheme is useful for polymerizing short DNA fragments for the mass production of peptides.

Another scheme for forcing directional ligation is to devise synthetic linkers or adapters that are used to create asymmetric cohesive ends. For example, Taylor and Hagerman, Gene 53:139 (1987), modified by Hartley-Gregori approach by attaching synthetic directional adapters to a DNA fragment in order to establish complete control over fragment orientation during ligation. Following polymerization, the multimers were ligated to a linearized vector suitable for E. coli transformation. Ståhl et al., Gene 89:187 (1990), described a similar method for polymerizing DNA fragments in a head-to-tail arrangement. Here, synthetic oligonucleotides were designed to encode an epitope-bearing peptide with 5'-protruding ends complementary to the asymmetric cleavage site of the class IIS restriction enzyme, BspMI. After polymerization, the peptide-encoding fragments were inserted into the unique BspMI site cleavage site of a vector, which was used to transform E. coli. Clones were screening using the polymerase chain reaction, and then subcloned into prokaryotic expression vectors for production of the peptides in E. coli.

In sum, methods that rely on in vivo gene amplification are not only time consuming, but also lack control over the final structure of the integrated and amplified gene. While in vitro gene amplification methods provide some control over the structure of the integrated gene, current methods typically require multiple cloning steps in prokaryotic hosts. In addition, presently described methods often require selection of transfected cells with a toxic drug that is rendered harmless by an enzyme product of a co-transfected gene. There is no assurance that cells possessing a sufficient level of this enzymatic activity also possess a sufficient number of copies of the desired gene to provide high levels of expression of the desired recombinant protein.

Despite advances in obtaining high levels of gene expression in recombinant host cells, therefore, a need still exists for a strategy that provides a rapid and simple method of producing high levels of recombinant protein in eukaryotic cells.

BRIEF SUMMARY OF THE INVENTION

The present invention provides improved methods for producing peptides, polypeptides, and proteins by recombinant host cells. According to one aspect of the present invention, nucleic acid molecules, which comprise amino acid encoding sequences, are polymerized in vitro. The polymerized nucleic acid molecules are then introduced into eukaryotic cells without the need for propagation in a prokaryotic host.

DESCRIPTION OF THE INVENTION

1. Overview

As described herein, the present invention provides methods for producing a nucleic acid polymer suitable for expression of an amino acid sequence of interest, comprising: (a) cleaving two or more expression vectors to produce either non-palindromic ends or palindromic ends, wherein cleaved expression vectors with palindromic ends are further treated to produce non-palindromic ends, wherein the expression vectors comprise an expression cassette that comprises a gene of interest and a selectable marker gene, and (b) ligating cleaved expression vectors with non-palindromic ends to produce nucleic acid polymers. Expression vectors comprising palindromic ends can be treated to produce non-palindromic ends by incubating expression vectors with an enzyme that provides a 3'-exonuclease activity. A 3'-exonuclease activity can be provided by T4 DNA polymerase, E. coli DNA polymerase I, Klenow fragment of DNA polymerase I, DEEP VENT DNA polymerase, VENT DNA polymerase, and the like.

Such methods can further comprise the act of fragmenting the nucleic acid polymer using mechanical shearing. In other variations, such methods further comprise the act of adding poison oligonucleotides to cleaved expression vectors with non-palindromic ends before the act of ligating, wherein the poison oligonucleotides are complementary to the non-palindromic ends of the cleaved expression vectors.

In certain variations of these methods, nucleic acid polymers comprise multiple copies of the gene of interest and the selectable marker gene in a 1:1 ratio. In addition, expression vectors can comprise a polycistronic transcription unit.

Suitable selectable marker genes include nucleotide sequences that encode a titratable protein. For example, the selectable marker gene product can be titratable with a toxic molecule. Suitable selectable marker genes include a *bleomycin-resistance* gene, a *metallothionein* gene, a *hygromycin B-phosphotransferase* gene, the AURI gene, an *adenosine deaminase* gene, an *aminoglycoside phosphotransferase* gene, a *dihydrofolate reductase* gene, a *thymidine kinase* gene, a *xanthine-guanine phosphoribosyltransferase* gene, and the like. Additional examples of titratable proteins include green fluorescent protein, red fluorescent protein, alkaline phosphatase, CD4, CD8, Class I major histocompatibility complex protein, and the like.

Expression vectors can be cleaved with a class IIS restriction enzyme to provide non-palindromic ends. Suitable class IIS restriction enzymes include AccB7I, AceIII, AclWI, AdeI, AhdI, Alw26I, AlwI, AlwNI, ApaBI, AspEI, AspI, AsuHPI, BbsI, BbvI, BbvII, Bce83I, BcefI, BciVI, BfiI, BglI, BinI, BmrI, BpiI, BpmI, BpuAI, BsaI, Bse3DI, Bse4I, BseGI, BseLI, BseRI, BsgI, BslI, BsmAI, BsmBI, BsmFI, BspMI, BsrDI, Bst71I, BstAPI, BstF5I, BstXI, Bsu6I, DraIII, DrdI, DseDI, Eam1104I, Eam1105I, EarI, EchHKI, Eco31I, Eco57I, EcoNI, Esp1396I, Esp3I, FokI, FauI, GsuI, HgaI, HphI, MboII, MsiYI, MwoI, NruGI, PflMI, PflFI, PleI, SfaNI, TspRI, Ksp632I, MmeI, RleAI, SapI, SfiI, TaqII, Tth111I, Tth111II, Van91I, XagI, and XcmI.

Additional enzymes that can be used to produce non-palindromic ends include AvaI, Ama87I, BcoI, BsoBI, Eco88I, AvaII, Eco47I, Bme18I, HgiEI, SinI, BanI, AccB1I, BshNI, Eco64I, BfmI, BstSFI, SfcI, Bpu10I, BsaMI, BscCI, BsmI, Mva1269I, Bsh1285I, BsaOI, BsiEI, BstMCI, Bse1I, BseNI, BsrI, Cfr10I, BsiI, BssSI, Bst2BI, BsiZI, AspS9I, Cfr13I, Sau96I, Bsp1720I, BlpI, Bpu1102I, CelII, Bst4CI, BstDEI, DdeI, CpoI, CspI, RsrII, DsaI, BstDSI, Eco24I, BanII, EcoT38I, FriOI, HgiJII, Eco130I, StyI, BssT1I, EcoT14I, ErhI, EspI, BlpI, Bpu1102I, Bsp1720I, CelII, HgiAI, BsiHKAI, Alw21I, AspHI, Bbv12I, HinfI, PspPPI, PpuMI, Psp5II, SanDI, SduI, Bsp1286I, BmyI, SecI, BsaJI, BseDI, SfcI, BfmI, BstSFI, and SmlI.

The present invention further provides methods for producing a recombinant eukaryotic host cell that expresses a peptide or polypeptide of interest, comprising: (a) cleaving at least two expression vectors to produce either non-palindromic ends or palindromic ends, wherein cleaved expression vectors with palindromic ends are further treated to produce non-palindromic ends, and wherein the expression vector comprises an expression cassette that comprises a gene of interest and a selectable marker gene, (b) ligating cleaved expression vectors with non-palindromic ends to produce nucleic acid polymers, (c) introducing the nucleic acid polymers into a eukaryotic host cell, and (d) culturing the recombinant eukaryotic host cell, which produces the peptide or polypeptide of interest. In certain variations of these methods, the nucleic acid polymers comprise multiple copies of the gene of interest and the selectable marker gene in a 1:1 ratio. Suitable eukaryotic host cells include a mammalian cell, a fungal cell, an insect cell, and an avian cell.

The present invention also includes, methods for producing a recombinant eukaryotic host cell that expresses a peptide or polypeptide of interest, comprising introducing a nucleic acid polymer into a eukaryotic host cell, wherein the nucleic acid polymer comprises multiple expression cassettes with head-to-tail orientations, wherein each expression cassette comprises a gene of interest and a selectable marker gene. In particular embodiments, the nucleic acid polymer comprises multiple copies of the gene of interest and a selectable marker gene in an approximate 1:1 ratio. An illustrative selectable marker gene is a nucleotide sequence that encodes a protein that is titratable.

The present invention further includes methods for producing recombinant host cells by introducing a nucleic acid polymer that comprises expression cassettes, but that lacks prokaryotic vector sequences. The present invention also provides nucleic acid polymers, comprising multiple copies of expression cassettes.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' (SEQ ID NO:1) is complementary to 5' CCCGTGCAT 3' (SEQ ID NO:2).

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "structural gene" refers to a nucleic acid molecule that is transcribed into messenger RNA (mRNA), which is then translated into a sequence of amino acids characteristic of a specific polypeptide. A "gene of interest" can be a structural gene.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules with free 5' and 3' ends. Linear DNA can be prepared from closed circular DNA molecules, such as plasmids, by enzymatic digestion or physical disruption.

"Directional ligation" refers to a method of producing a nucleic acid polymer comprising monomers arranged in a fixed orientation. For example, directional ligation can be used to produce a polymer comprising tandem repeats of monomers with head-to-tail orientations.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the term "multiple" or "multimeric" refers to two or more copies of a gene of interest, such as 2 to 50 copies, 2 to 30 copies, 2 to 20 copies, 2 to 15 copies, or 2 to 10 copies. Further exemplary ranges include 3 to 20 copies, 3 to 15 copies, or 3 to 10 copies. Conveniently, a construct can comprise 3 or more copies (e.g., 3 to 7, or 5 to 7). Ranges of 7 or more, for example 7 to 30 copies, 7 to 20 copies, or 7 to 15 copies, may also be useful.

A "polycistronic transcription unit" is a transcription unit in which more than one gene is under the control of the same promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins, colony stimulating factors, interferons, stem cell growth factors, erythropoietin, and thrombopoietin.

An "anti-idiotype antibody" is an antibody that binds with the variable region domain of an immunoglobulin.

An "antibody fragment" is a portion of an antibody such as $F(ab')_2$, $F(ab)_2$, Fab', Fab, and the like. Regardless of structure, an antibody fragment binds with the same antigen that is recognized by the intact antibody.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

A "fusion protein" is a hybrid protein expressed by a nucleic acid molecule comprising nucleotide sequences of at least two genes.

The term "antibody fusion protein" refers to a recombinant molecule that comprises an antibody, or antibody fragment, and a therapeutic agent. Examples of therapeutic agents suitable for such fusion proteins include immunomodulators ("antibody-immunomodulator fusion protein") and toxins ("antibody-toxin fusion protein"). Illustrative toxin components include a *Pseudomonas* exotoxin moiety, a diphtheria toxin moiety, an RNase moiety, a DNase I moiety, a gelonin moiety, and a *Staphylococcal* enterotoxin-A moiety.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

An "antigenic peptide" is a peptide that will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell, which binds or expresses the antigen. The antigenic peptide can be bound in the context of a class I or class II major histocompatibility complex molecule on an antigen presenting cell or on a target cell.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of a Nucleic Acid Polymer Containing Multiple Copies of a Gene of Interest According to the present invention, cells are transfected with a nucleic acid polymer that comprises multiple expression cassettes, which reside in the same orientation. The generation of such a tandem array maximizes the stability of the polymer following integration into the genomic DNA of the host cell. Each expression cassette comprises: (1) a nucleotide sequence that encodes an amino acid sequence of interest, which is referred to as the "gene of interest," and (2) a nucleotide sequence that encodes a selectable marker. Suitable selectable marker genes include those that encode a protein that is titratable by a drug, as described below. The advantage of such marker genes is that the level of drug resistance of the host cell provides an indication of the level of selectable marker gene expression.

Nucleic acid polymers can be characterized by a ratio for the gene of interest:selectable marker gene that is X:Y, wherein X is an integer from 1 to 10 when Y has a value of 1, and wherein Y is an integer from 1 to 10 when X has a value of 1. In either case, the range of values from 1 to 10 includes subranges, such as 2 to 9, 3 to 8, 4 to 7, 5 to 6, 2 to 6, 5 to 10, and the like.

Certain nucleic acid polymers are characterized by having a 1:1 ratio for the gene of interest:selectable marker gene. Since the relative amount of the gene of interest and the selectable marker gene is predetermined, drug resistance also provides a measure of the level of expression of the desired protein. This relationship between the expression of the selectable marker gene and the gene of interest is stronger when the selectable marker gene product is a protein titratable by a drug.

A. Expression Cassette Design

An expression cassette comprises a gene of interest and a selectable marker gene. The gene of interest can encode any desired amino acid sequence. Exemplary amino acid sequences include proteins, polypeptides, peptides, and fusion proteins. Polypeptides can consist of about 10 to about 20 amino acids, about 20 to about 40 amino acids, about 40 to about 100 amino acids, or greater than 100 amino acids.

Illustrative proteins include antibodies and antibody fragments, receptors, hormones, and other proteins having potential industrial or therapeutic value. For example, an expression cassette can include a nucleic acid molecule that encodes a pharmaceutically active molecule, such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21), colony stimulating factors (e.g., granulocyte-colony stimulating factor, and granulocyte macrophage-colony stimulating factor), interferons (e.g., interferons-α, -β, -γ, -ω, -δ, -τ, and -ε), a stem cell growth factor, erythropoietin, and thrombopoietin. Additional examples of a protein of interest include an antibody, an antibody fragment, an anti-idiotype antibody (or, fragment thereof), a chimeric antibody, a humanized antibody, an antibody fusion protein, and the like.

Recombinant host cells can be produced that secrete the desired protein into surrounding medium. Accordingly, the present invention contemplates expression cassettes comprising a nucleotide sequence encoding a secretory signal sequence, which is also known as a "signal peptide," a "leader sequence," a "prepro sequence," or a "pre sequence." The secretory signal sequence is operably linked to a gene of interest such that the two sequences are joined in the correct reading frame and positioned to direct the newly synthesized protein of interest into the secretory pathway of the host cell. Secretory signal sequences are commonly positioned 5' to the nucleotide sequence encoding the amino acid sequence of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of a protein produced by mammalian cells (e.g., tissue-type plasminogen activator signal sequence, as described, for example, in U.S. Pat. No. 5,641,655) is useful for expression of gene of interest in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, 2$^{nd}$ Edition, Glover and Hames (eds.), pages 123–167 (Oxford University Press 1995).

Expression cassettes can also comprise nucleotide sequences that encode a peptide tag to aid the purification of the desired protein. Peptide tags that are useful for isolating recombinant polypeptides include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

A wide variety of selectable marker genes are available (see, for example, Kaufman, *Meth. Enzymol.* 185:487 (1990); Kaufman, *Meth. Enzymol.* 185:537 (1990)). In the present context, a suitable selectable marker is "titratable," in that the resistance of a cell to a high dose of toxic drug will be related to the number of selectable marker proteins produced by the cell. This characteristic is lacking when the selectable marker is an enzyme that can neutralize a high number of toxic drug molecules per enzyme.

Ble genes, such as the Sh ble gene, are particularly useful selectable marker genes for the presently described methods. These genes produce a protein that inhibits the activity of bleomycin/phleomycin-type drugs, such as ZEOCIN (Gatignol et al., *Mol. Gen. Genet.* 207:342 (1987); Drocourt et al., *Nucl. Acids Res.* 18:4009 (1990)). The protein coded by a bleomycin-resistance gene binds a bleomycin-type drug in a one to one ratio, resulting in a sequestering of the toxic drug (see, for example, Gatignol et al., *FEBS Lett.* 230:171 (1988)). In addition to the stoichiometric binding, another advantage of this system is that ZEOCIN is toxic in a broad range of cell types, including bacteria, fungi, plant, avian, insect, and mammalian cells.

Metallothionein genes encode proteins that have a high affinity for toxic metals, such as cadmium, zinc, and copper (Beach and Palmiter, *Proc. Nat'l Acad. Sci. USA* 78:2110 (1981); Huang et al., *EXS* 52:439 (1987); Czaja et al., *J. Cell. Physiol.* 147:434 (1991)). Accordingly, metallothionein genes provide suitable titratable markers for the methods described herein.

Additional selectable markers include hygromycin B-phosphotransferase, the AUR1 gene product, adenosine deaminase, aminoglycoside phosphotransferase, dihydrofolate reductase, thymidine kinase, and xanthine-guanine phosphoribosyltransferase (see, for example, Srivastava and Schlessinger, *Gene* 103:53 (1991); Romanos et al., "Expression of Cloned Genes in Yeast," in *DNA Cloning 2: Expression Systems, 2nd Edition*, pages 123–167 (IRL Press 1995); Markie, *Methods Mol. Biol.* 54:359 (1996); Pfeifer et al., *Gene* 188:183 (1997); Tucker and Burke, *Gene* 199:25 (1997); Hashida-Okado et al., *FEBS Letters* 425:117 (1998)).

When such selectable marker genes are used with the present methods, a toxic drug is preferably chosen that inhibits the enzymatic activity of the gene product to provide the titratable characteristic. Such drugs include molecules that bind with the selectable marker gene product with high affinity or even covalently. For example, 2,4-diamino-5-[3,5-dimethoxy-4-(p-bromoacetamidophenoxy)benzyl] pyrimidine irreversibly inhibits *Neisseria gonorrhoeae* dihydrofolate reductase (Tansik et al., *J. Biol. Chem.* 259:12299 (1984)). Moreover, Rosowsky et al., *J. Med. Chem.* 30:1463 (1987), described a method for preparing methotrexate analogs with strong alkylating activity by replacing the L-glutamate side chain with N omega-haloacetyl derivatives of L-lysine and L-ornithine. N epsilon-(bromoacetyl)-L-lysine and N delta-(bromoacetyl)-L-ornithine analogs gave results consistent with covalent binding to dihydrofolate reductase of *Candida albicans* and murine leukemia cells. Additional examples include adenosine deaminase inhibitors, such as erythro-9-(2-hydroxy-3-nonyl)adenine (EHNA) analogs, including 9'-chloro-EHNA and 9'-phthalimido-EHNA (Barankiewicz et al., *J. Pharmacol. Exp. Ther.* 283:1230 (1997)). Other suitable toxic drugs are known to those of skill in the art.

An alternate approach is to use a selectable marker gene that encodes a mutated enzyme that is less active than the corresponding wild-type enzyme. As an illustration, Munir et al., *Protein Eng.* 7:83 (1994), describe the design of mutant thymidine kinase enzymes with decreased activity (also see Liu and Summers, *Virology* 163:638 (1988); Mendel et al., *Antimicrob. Agents Chemother.* 39:2120 (1995)). Low activity mutants have also been described for adenosine deaminase and dihydrofolate reductase (see, for example, Prendergast et al., *Biochemistry* 27:3664 (1988); Jiang et al., *Hum. Mol. Genet.* 6:2271 (1997); Ercikan-Abali et al., *Mol. Pharmacol.* 49:430 (1996)).

Another type of selectable marker gene is a gene that produces a readily detectable protein, such as green fluorescent protein, red fluorescent protein, an enzyme (e.g., placental alkaline phosphatase), or a cell surface protein that can be detected with an antibody (e.g. CD4, CD8, Class I major histocompatibility complex (MHC) protein, etc.). The expression products of such selectable marker genes can be used to sort transfected cells from untransfected cells by such standard means as FACS sorting or magnetic bead separation technology.

Nucleic acid molecules encoding an amino acid sequence of interest or a selectable marker can be obtained by screening a human cDNA or genomic library using standard techniques. Alternatively, such genes can be obtained by synthesizing nucleic acid molecules using mutually priming long oligonucleotides, or by chemical DNA synthesis. In addition, many suitable protein-encoding nucleic acid molecules are commercially available.

To express a gene of interest or a selectable marker gene, a nucleic acid molecule encoding the amino acid sequence must be operably linked to regulatory sequences that control transcriptional expression and then, introduced into a host cell. In addition to transcriptional regulatory sequences, such as promoters and enhancers, expression vectors can include transcriptional and translational regulatory sequences. For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Suitable transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control expression of the gene of interest in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In particular expression cassettes, the nucleotide sequence that resides upstream of the initiation codon of the selectable marker gene is mutagenized to provide a context that is unfavorable to translation initiation. The objective of this type of alteration is to reduce the expression level of the selectable marker gene per expression unit. In this way, a high level of expression of the selectable marker gene more accurately reflects the number of in vitro amplified units carried by the host cell.

For example, at least one of the -3, -6, and -9 positions can be mutated to a thymidine nucleotide. Moreover, adenine or cytidine nucleotides, which reside in at least one of positions -1, -2, -4, and -5, can be mutated to guanosine or thymidine nucleotides to further reduce the efficiency of translation initiation. The nucleotide sequence, 5' . . . TCCTGTTGT ATG . . . 3' (SEQ ID NO:3), is one example of a nucleotide sequence, which can reside upstream of an initiation codon, provide decreased efficiency of translation initiation. Additional nucleotide sequence modifications can be devised by those of skill in the art.

In another variation, a nucleotide sequence can be included that flanks the expression cassette to isolate the introduced sequences from undesired regulatory effects of cellular chromatin. As an illustration, such an insulator sequence can be placed upstream of a CMV promoter. See, for example, Chung et al., *Cell* 74:505 (1993).

It may be advantageous for recombinant host cells to express certain selectable marker gene products on the cell surface. For example, green fluorescent protein can be expressed on the cell surface. Various approaches can be used to achieve surface display by producing fusion proteins that contain the selectable marker protein and a transmembrane domain from another protein to anchor the fusion protein to the cell membrane. As an illustration, pDisplay™ is a commercially available vector that is used to display a polypeptide on the surface of a mammalian cell (INVITROGEN Corp.; Carlsbad, Calif.). In this vector, a multiple cloning site resides between sequences that encode two identifiable peptides, hemagglutinin A and myc epitopes. The vector also includes sequences that encode an N-terminal signal peptide derived from a murine immunoglobulin k-chain, and a type I transmembrane domain of platelet-derived growth factor receptor, located at the C-terminus. In this way, a selectable marker gene product is expressed by a transfected cell as an extracellular fusion protein, anchored to the plasma membrane at the fusion protein C-terminus by the transmembrane domain.

Alternatively, a type II signal anchor domain-encoding nucleotide sequence can be used to provide surface display of the selectable marker gene product. Examples of type II cell surface proteins that comprise such signal anchor domains include influenza neuraminidase, the small hydrophobic proteins of the paramyxovirus simian virus, the paramyxovirus hemagglutinin-neuraminidase, human and rat asialoglycoprotein receptors, chicken hepatic lectin, human and rabbit neutral endopeptidase, human intestinal aminopeptidase, rabbit sucrase-isomaltase receptor, human transferrin receptor, hepatic glycoprotein receptor, human IgE receptor, murine 1,4-β-galactosyltransferase, human P-glycoprotein receptor, human invariant chains of class II histocompatibility antigens, rat sodium channel proteins, rat brain, muscle and liver glucose transporter proteins, bacterial leader peptidase, and members of the tumor necrosis factor/nerve growth factor superfamily (see, for example, Wolfe et al., *J. Biol. Chem.* 258:12073 (1983); Chiacchi and Drickamer, *J. Biol. Chem.* 259:15440 (1984); Hiebert et al., *J. Virol.* 54:1 (1985); Hiebert et al., *J. Virol.* 55:744 (1985); Schneider et al., *Nature* 311:675 (1984); Spiess and Lodish, *Proc. Nat'l Acad. Sci. USA* 82:6465 (1985); Strubin et al., *EMBO J.* 3:869 (1984); Semenza, *Annu. Rev. Cell Biol.* 2:255 (1986); Lipp and Dobberstein, *J. Cell Biol.* 106:1813 (1988); Hartmann et al., *Proc. Nat'l Acad. Sci. USA* 86:5786 (1989)). Moreover, Chou and Elrod, *Proteins: Structure, Function, and Genetics* 34:137 (1999), disclose 152 type II membrane proteins, which they used to devise a method for predicting whether an amino acid sequence confers the type II membrane protein structure.

Expression cassettes can be designed to comprise two "transcriptional units," each comprising a transcriptional regulatory element, a coding region, and a transcription terminator. In this system, one coding region encodes the amino acid sequence of interest, while the second coding region encodes the selectable marker. Both transcriptional units can contain the same transcriptional regulatory element.

Alternatively, an expression cassette can comprise regions that encode the amino acid sequence of interest and a selectable marker, wherein the coding regions reside between a transcriptional regulatory element and a transcription terminator, if each of the coding regions has its own ribosome binding site (see, for example, Lee et al., *Nucl. Acids Res.* 12:6797 (1984)). Such an expression cassette comprises a polycistronic transcription unit. As an illustration, an expression cassette can comprise an internal ribosome entry site-linked selectable marker gene, which resides downstream of the coding region for the amino acid sequence of interest.

B. Design of Vector Comprising an Expression Cassette

Expression vectors that are suitable for production of a desired protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; (3) DNA elements that control the processing of transcripts, such as a transcription termination/polyadenylation sequence; and (4) a selectable marker gene for eukaryotic cells. As discussed above, expression vectors can also include nucleotide sequences encoding a secretory sequence that directs the heterologous polypeptide into the secretory pathway of a host cell. Moreover, vectors for high level expression in yeast can include targeting sequences to promote homologous recombination in host genomic DNA.

In addition, an expression vector suitable for use in the methods described herein may contain at least one cleavage site that provides non-palindromic ends. Sequences recognized by restriction enzymes are typically completely symmetrical inverted repeats, known as palindromes. That is, the order of the bases is the same when the two strands of the palindrome are read in opposite directions. Palindromic termini are self-complementary and can self-ligate, or ligate to an identical terminus facing the opposite way. Consequently, self-ligation of vectors with palindromic termini will produce polymers containing units orientated in mixed directions.

Restriction endonucleases belong to three general classes. Class I restriction endonucleases cleave at widely varying distances from their recognition sites. Class II restriction endonucleases cleave within their recognition sites, while a subclass, class IIS, cleaves at precise distances outside of their recognition sites. Like class IIS enzymes, class III enzymes have separate recognition and cleavage domains. However, the class IIS restriction enzymes and methyltransferases are separate molecules, whereas for class III they form a single multidomain moiety.

Since the recognition and cleavage sites are the same for class II enzymes and distinct for class IIS enzymes, the products of these two classes have different properties. Class II enzymes cleave within a symmetric recognition site, producing 5' to 3' sequences that are identical for both strands. For example, EcoRI cleaves as follows:

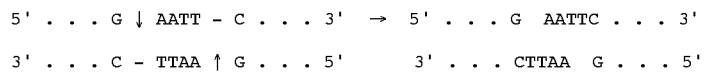

In contrast, a class IIS restriction endonuclease cleaves outside an asymmetric recognition site at a precise distance from the site. Due to this asymmetry, the 5' to 3' recognition sequences are different for each strand. For example, BstXI cleaves the following sequence (CCANNNNNNTGG (SEQ ID NO:4)/GGTNNNNNNACC (SEQ ID NO:5)), where "N" is any nucleotide:

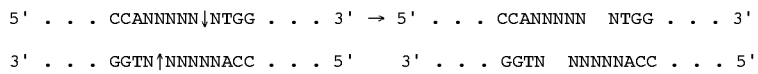

When DNA fragments containing these non-palindromic, or "rotationally nonequivalent," ends are ligated to each other, the fragments are inserted directionally.

Suitable class IIS restriction enzymes include those enzymes that recognize a five-base contiguous sequence, such as the following enzymes and their isoschizomers, which are indicated in parentheses: Alw26I (BsmAI), AlwI (AclWI, BinI), AsuHPI (HphI), BbvI (Bst71I), BcefI, BstF5I (BseGI, FokI), FauI, HgaI, MboII, PleI, SfaNI, and TspRI. The following class IIS enzymes that recognize a six-base contiguous sequence can also be used: AceIII, BbsI (BbvII, BpiI, BpuAI), Bce83I, BciVI, BfiI (BmrI), BpmI (GsuI), BsaI (Eco31I), BseRI, BsgI, BsmBI (Esp3I), BsmFI, BspMI, BsrDI (Bse3DI), Bsu6I (Eam1104I, EarI, Ksp632I), Eco57I, FauI, MmeI, RleAI, TaqII, and Tth111 II. SapI, which recognizes a seven-base sequence, and SfiI, which recognizes an eight-base sequence, also can be used to cleave an expression vector. Further examples of useful enzymes include those that recognize a four-base pair split sequence (e.g., Bse4I (BseLI, MsiYI, BslI), MwoI), and enzymes that recognize a six-base pair split sequence (e.g., AccB7I (Esp1396I, PflMI, Van91I), AdeI (DraIII), AhdI (AspEI, Eam1105I, EchHKI, NruGI), AlwNI, ApaBI (BstAPI), AspI (PflFI, Tth111I), BglI, BstXI, DrdI (DseDI), EcoNI (XagI), XcmI). Additional suitable class IIS restriction enzymes are known to those of skill in the art (see, for example, Szybalski et al., *Gene* 100:13 (1991)).

There are other enzymes that are not class IIS enzymes, which produce non-palindromic ends. These are also suitable for the presently described methods. Examples of such enzymes include: AvaI (Ama87I, BcoI, BsoBI, Eco88I), AvaII (Eco47I, Bme18I, HgiEI, SinI), BanI (AccB1I, BshNI, Eco64I), BfmI (BstSFI, SfcI), Bpu10I, BsaMI (BscCI, BsmI, Mva1269I), Bsh1285I (BsaOI, BsiEI, BstMCI), Bse1I (BseNI, BsrI, Cfr10I), BsiI (BssSI, Bst2BI), BsiZI (AspS9I, Cfr13I, Sau96I), Bsp1720I (BlpI, Bpu1102I, CelII), Bst4CI, BstDEI (DdeI), CpoI (CspI, RsrII), DsaI (BstDSI), Eco24I (BanII, EcoT38I, FriOI, HgiJII), Eco130I (StyI, BssT1I, EcoT14I, ErhI), EspI (BlpI, Bpu1102I, Bsp1720I, CelII), HgiAI (BsiHKAI, Alw21I, AspHI, Bbv12I), HinfI, PspPPI (PpuMI, Psp5II), SanDI, SduI (Bsp1286I, BmyI), SecI (BsaJI, BseDI), SfcI (BfmI, BstSFI), and SmlI. Suitable enzymes recognize a six-base sequence, a seven-base sequence, or an eight-base sequence.

MI120, and B170 (see, for example, Hardy, "Bacillus Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, 3$^{rd}$ *Edition* (John Wiley & Sons 1995) ["Ausubel 1995"]; Wu et al., *Methods in Gene Biotechnology* (CRC Press, Inc. 1997)).

C. Generation of the Nucleic Acid Polymer

According to one approach, an expression vector is cleaved with a restriction enzyme to generate non-palindromic ends. In this way, subsequent ligation will produce a polymer comprising subunits having the same orientation.

It is also possible to cleave an expression vector with an enzyme that produces palindromic ends. However, the cleaved DNA should be treated to create non-palindromic ends. This objective can be achieved, for example, by treatment with an enzyme that provides a 3'-exonuclease activity. Illustrative enzymes include T4 DNA polymerase, *E. coli* DNA polymerase I, Klenow fragment of DNA polymerase I, DEEP VENT DNA polymerase, and VENT DNA polymerase.

For example, the 3'-exonuclease activity of T4 DNA polymerase can be used to generate non-palindromic ends from palindromic ends as described by Kuijper et al., *Gene* 112:147 (1992). As an illustration, a vector comprising the sequence, ACTGCACCGGAATTCTGTGCGTAGG (SEQ ID NO:6)/TGACGTGGCCTTAAGACACGCATCC (SEQ ID NO:7), can be cleaved with EcoRI to produce the following palindromic ends:

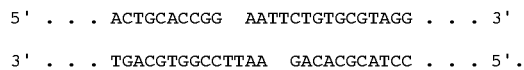

Treatment with T4 DNA polymerase in the presence of dTTP will remove nucleotides until the enzyme reaches a dT nucleotide. At this point, the enzyme will begin to alternate between a polymerase reaction and an exonuclease reaction. As a result, the following non-palindromic ends are obtained:

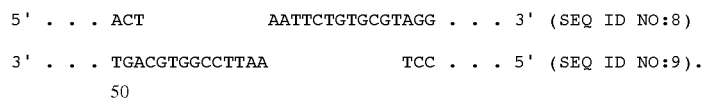

As an alternative, an expression vector can be used which lacks an enzyme cleavage site that will generate non-palindromic ends. In this case, suitable ends are generated with an enzyme having exonuclease activity, as described below.

After constructing the expression vector, the vector is propagated in a host cell to synthesize nucleic acid molecules for the generation of a nucleic acid polymer. Vector propagation is conveniently carried out in a prokaryotic host cell, such as *E. coli* or *Bacillus subtilus*. Suitable strains of *E. coli* include BL21(DE3), BL21(DE3)pLysS, BL21(DE3) pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, Expression vectors treated in this manner will only ligate as tandem repeats with head-to-tail orientations. Particular non-palindromic ends can be designed by selecting suitable deoxynucleotide for the exonuclease reaction.

Restriction enzymes and DNA polymerases can be inactivated by standard methods, including heat inactivation. Moreover, these enzymes can be removed from a mixture containing a cleaved DNA molecule by extraction with organic solutions, such as a phenol/chloroform solution and the like.

General methods for ligating nucleic acid molecules are known to those of skill in the art. See, for example, Ausubel et al. (eds.), *Short Protocols in Molecular Biology*, 3$^{rd}$ *Edition* (John Wiley & Sons 1995). Following polymerization, it may be desirable to decrease the size of the nucleic acid polymers. This can be achieved by fragmenting the nucleic acid polymer with mechanical shearing.

Alternatively, oligonucleotides can be added during ligation to limit the size of the nucleic acid polymers. In this approach, one end of the "poison oligonucleotide" has a sequence that is complementary to the cleaved vector, and can compete with another cleaved vector for ligation. The other end of the oligonucleotide lacks a complementary sequence to the cleaved vector sequence, and may also lack a phosphate group at the 5' end to support a ligation reaction. Therefore, the incorporation of a poison oligonucleotide by an elongating nucleic acid polymer inhibits further elongation of the polymer. In this way, the length of the nucleic acid polymer can be controlled by varying the molar ratio of poison oligonucleotide to cleaved vector in the ligation reaction.

Studies with poison oligonucleotides indicate that the number of vector units within a nucleic acid polymer will be proportional to the molar excess of vector unit to poison oligonucleotide. For example, a molar ratio of 1:100 (poison oligonucleotide:vector) appeared to have no inhibitory effect on vector polymerization. Doubling the amount of poison oligonucleotide also resulted in a high molecular weight polymer. In contrast, a molar ratio of 10:1 (poison oligonucleotide:vector) appeared to inhibit polymerization at a level of 90%. Those of skill in the art can perform similar studies to optimize polymerization for particular vectors or expression cassettes.

A poison oligonucleotide may be single-stranded or double-stranded. The double-stranded form minimizes potential secondary structure, which may reduce the accessibility of the complementary ends. A double-stranded poison oligonucleotide can be produced as two partially complementary oligonucleotides. The region of complementarity in a double-stranded poison oligonucleotide can vary from about 15 to about 30 base pairs in length to provide stability, and the sequence should lack palindromic sequences that would promote intra-strand hybrid formation. Single-stranded poison oligonucleotides should be less than ten nucleotides in length to minimize potential secondary structure, which would reduce the accessibility of the complementary end.

Poison oligonucleotides can be synthesized using standard techniques. For example, a poison oligonucleotide can be produced as two partially complementary oligonucleotides, which are denatured by heating to 90° C. and annealed to a double strand conformation under conditions, which favor DNA hybridization. A suitable condition would be 72° C. in the presence of 10 mM NaCl, pH 8.0.

The present invention also includes the production of heteropolymers that comprise expression vectors containing different genes. As an illustration, it may be necessary to transfect cells with genes that encode post-translational processing enzymes for the protein of interest. In this case, linearized expression vectors that include genes for the appropriate enzymes can be ligated to produce a heteropolymer. The processing genes can be controlled by similar regulatory elements. Moreover, the relative amounts of the genes can be controlled by altering the ratios of the various expression vectors. Similarly, heteropolymers can be devised to provide expression of subunits of a multimeric protein, or to provide a recombinant host cell with multiple members of a metabolic pathway, which can modify the properties of the host cell.

Another form of heteropolymer comprises two types of expression cassettes, each comprising a nucleotide sequence that encodes the same amino acid sequence of interest, which contain different selectable marker genes. In this case, recombinant host cells are selected for high expression of the desired amino acid sequence by a high level expression of both selectable marker genes. Such a heteropolymer need not include vector sequences. That is, the heteropolymer can be produced by polymerization of expression cassettes.

According to another general approach, expression cassettes are polymerized to provide a nucleic acid polymer for transfection of eukaryotic cells. Such a nucleic acid polymer can lack any vector nucleotide sequence. Typically, it is necessary to propagate a vector in a bacterial or other intermediate cell to produce sufficient nucleic acid for introduction into the host cell, which is used for the expression of the recombinant protein. This procedure, however, has several disadvantages.

(1) The expression vector contains bacterial sequences, such as a drug resistance marker for selection in microbial cells and a microbial origin for DNA replication. These sequences, which are usually not required in the production host cell, may be inhibitory to some cells, or decrease the stability of the DNA in the producing host cell.

(2) The presence of microbial DNA in the eukaryotic host cell reduces the number of copies of recombinant protein-encoding sequences that can be carried by the producing host cell.

(3) Since the microbial drug selection marker and expression cassette reside within the vector, it is not possible to vary the ratio of these elements with respect to each other. This may present a problem if the selection marker protein is cytotoxic to a eukaryotic host when accumulated at high levels. Therefore, it may be advantageous to decrease the ratio of drug selection marker to expression cassette to increase the yield of the recombinant protein.

(4) Another consequence of using DNA elements operationally linked on the same vector is that any modification to the elements or the introduction, replacement, deletion or reshuffling of the elements will necessitate reconstruction of the entire plasmid and DNA prepared before introduction into host cells. Subsequently, is not convenient to make multiple variants of the vector to improve yield of recombinant protein.

Hence, there is need for a convenient method to make multiple variants of a nucleic acid polymer that comprises expression cassettes, and that is free of extraneous vector sequences, as well as a need for a simple means to vary the ratio, relative order, and composition of functional elements. For example, a collection of functional nucleic acid elements can be synthesized by PCR, or excised from plasmids. It is then possible to engineer, onto the ends of these elements, a series of non-nonpalidromic cohesive ends, which mediate ligation of the elements in a defined and predictable composition. In this way, a multiplicity of nucleic acid polymers with useful functions can be easily constructed and introduced into host cells. Since the nucleic acid polymer is not propagated in a bacterial or other intermediate cell before introduction into the final eukaryotic host cell, the DNA polymer need not include DNA replication or selection elements that provide no useful function in the eukaryotic host cells.

4. Production of Recombinant Protein by Host Cells

The protein of interest may be expressed in any prokaryotic or eukaryotic host cell. The protein of interest can be produced by a eukaryotic cell, such as a mammalian cell, fungal cell, insect cell, avian cell, and the like. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

A nucleic acid polymer can be introduced into host cells using a variety of standard techniques including calcium phosphate transfection, liposome-mediated transfection, microprojectile-mediated delivery, electroporation, and the like. Transfected cells can be selected and propagated to provide recombinant host cells that comprise the gene of interest stably integrated in the host cell genome.

The baculovirus system provides an efficient means to introduce cloned genes of interest into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zace2 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed polypeptide, for example, a Glu-Glu epitope tag (Grussenmeyer et al., *Proc. Nat'l Acad. Sci.* 82:7952 (1985)). Using a technique known in the art, a transfer vector containing a gene of interest is transformed into *E. coli*, and screened for bacmids, which contain an interrupted lacZ gene indicative of recombinant baculovirus. The bacmid DNA containing the recombinant baculovirus genome is then isolated using common techniques.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems,: 2nd Edition*, Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Fungal cells, including yeast cells, can also be used to express the genes of interest. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat No. 4,931,373, Brake, U.S. Pat No. 4,870,008, Welch et al., U.S. Pat No. 5,037,743, and Murray et al., U.S. Pat No. 4,845, 075. Transformed cells are selected by phenotype determined by the selectable marker, commonly drug resistance or the ability to grow in the absence of a particular nutrient (e.g., leucine). An illustrative vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat No. 4,599,311, Kingsman et al., U.S. Pat No. 4,615,974, and Bitter, U.S. Pat No. 4,977,092) and alcohol dehydrogenase genes. See also U.S. Pat. Nos. 4,990,446, 5,063,154, 5,139, 936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. For large-scale, industrial processes where it is desirable to minimize the use of methanol host cells can be used in which both methanol utilization genes (AUG1 and AUG2) are deleted. For production of secreted proteins, host cells can be used that are deficient in vacuolar protease genes (PEP4 and PRB1). Electroporation is used to facilitate the introduction of a plasmid containing DNA encoding a polypeptide of interest into P. methanolica cells. P. methanolica cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Nucleic acid polymers can also be introduced into plant protoplasts, intact plant tissues, or isolated plant cells. Methods for introducing nucleic acid molecules into plant tissue include the direct infection or co-cultivation of plant tissue with Agrobacterium tumefaciens, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Standard methods for introducing nucleic acid molecules into bacterial, yeast, insect, mammalian, and plant cells are provided, for example, by Ausubel (1995). General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Established methods for isolating recombinant proteins from a baculovirus system are described by Richardson (ed.), *Baculovirus Expression Protocols* (The Humana Press, Inc. 1995).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for producing a nucleic acid polymer suitable for expression of an amino acid sequence of interest, comprising:
   (a) cleaving two or more expression vectors to produce either non-palindromic ends or palindromic ends, wherein cleaved expression vectors with palindromic ends are further treated to produce non-palindromic ends, wherein the expression vectors comprise an expression cassette that comprises a gene of interest and a selectable marker gene, and
   (b) ligating cleaved expression vectors with non-palindromic ends to produce nucleic acid polymers; and
   (c) adding poison oligonucleotides to the cleaved expression vectors having non-palindromic ends before the act of ligating, wherein the poison oligonucleotides are complementary to the non-palindromic ends of the cleaved expression vectors.

2. The method of claim 1, wherein the nucleic acid polymers comprise multiple copies of the gene of interest and the selectable marker gene in a 1:1 ratio.

3. The method of claim 1, further comprising the act of fragmenting the nucleic acid polymer using mechanical shearing.

4. The method of claim 1, wherein expression vectors comprising palindromic ends are treated to produce non-palindromic ends by incubating the expression vectors having palindromic ends with an enzyme that provides a 3'-exonuclease activity.

5. The method of claim 4, wherein the 3'-exonuclease activity-providing enzyme is selected from the group consisting of T4 DNA polymerase, *E. coli* DNA polymerase I, Klenow fragment of DNA polymerase I, DEEP VENT DNA polymerase, and VENT DNA polymerase.

6. The method of claim 1, wherein the expression vectors comprise a polycistronic transcription unit.

7. The method of claim 1, wherein the selectable marker gene encodes a protein that is titratable.

8. The method of claim 7, wherein the selectable marker gene product is titratable with a toxic molecule.

9. The method of claim 8, wherein the selectable marker gene is selected from the group consisting of a *bleomycin-resistance* gene, a *metallothionein* gene, a *hygromycin B-phosphotransferase* gene, the *AUR1* gene, an *adenosine deaminase* gene, an *aminoglycoside phosphotransferase* gene, a *dihydrofolate reductase* gene, a *thymidine kinase* gene, and a *xanthine-guanine phosphoribosyltransferase* gene.

10. The method of claim 7, wherein the selectable marker gene encodes a protein selected from the group consisting of green fluorescent protein, red fluorescent protein, alkaline phosphatase, CD4, CD8, and Class I major histocompatibility complex protein.

11. The method of claim 1, wherein the expression vectors are cleaved with a class IIS restriction enzyme to provide non-palindromic ends.

12. The method of claim 11, wherein the class IIS restriction enzyme is selected from the group consisting of AccB7I, AceIII, AclWI, AdeI, AhdI, Alw26I, AlwI, AlwNI, ApaBI, AspEI, AspI, AsuHPI, BbsI, BbvI, BbvII, Bce83I, BcefI, BciVI, BfiI, BglI, BinI, BmrI, BpiI, BpmI, BpuAI, BsaI, Bse3DI, Bse4I, BseGI, BseLI, BseRI, BsgI, BsII, BsmAI, BsmBI, BsmFI, BspMI, BsrDI, Bst71I, BstAPI, BstF5I, BstXI, Bsu6I, DraIII, DrdI, DseDI, Eam1104I, Eam1105I, EarI, EchHKI, Eco31I, Eco57I, EcoNI, Esp1396I, Esp3I, FokI, FauI, GsuI, HgaI, HphI, MboII, MsiYI, MwoI, NruGI, PflMI, PflFI, PleI, SfaNI, TspRI, Ksp632I, MmeI, RleAI, SapI, SfiI, TaqII, Tth111I, Tth111II, Van91I, XagI, and XcmI.

13. The method of claim 1, wherein the expression vectors are cleaved to produce non-palindromic ends, using an enzyme selected from the group consisting of AvaI, Ama87I, BcoI, BsoBI, Eco88I, AvaII, Eco47I, Bme18I, HgiEI, SinI, BanI, AccB1I, BshNI, Eco64I, BfmI, BstSFI, SfcI, Bpu10I, BsaMI, BscCI, BsmI, Mva1269I, Bsh1285I, BsaOI, BsiEI, BstMCI, Bse1I, BseNI, BsrI, Cfr10I, BsiI, BssSI, Bst2BI, BsiZI, AspS9I, Cfr13I, Sau96I, Bsp1720I, BlpI, Bpu1102I, CelII, Bst4CI, BstDEI, DdeI, CpoI, CspI, RsrII, DsaI, BstDSI, Eco24I, BanII, EcoT38I, FriOI, HgiJII, Eco130I, StyI, BssT1I, EcoT14I, ErhI, EspI, BlpI, Bpu1102I, Bsp1720I, CelII, HgiAI, BsiHKAI, Alw21I, AspHI, Bbv12I, HinfI, PspPPI, PpuMI, Psp5II, SanDI, SduI, Bsp1286I, BmyI, SecI, BsaJI, BseDI, SfcI, BfmI, BstSFI, and SmlI.

* * * * *

SEQUENCE LISTING

```
<160> NUMBER OF SEQ ID NOS: 9

<210> SEQ ID NO 1
<211> LENGTH: 9
<212> TYPE: DNA
<213> ORGANISM: Artificial Sequence
<220> FEATURE:
<223> OTHER INFORMATION: Illustrative nucleotide sequence.

<400> SEQUENCE: 1 atgcacggg                                                              9

<210> SEQ ID NO 2
<211> LENGTH: 9
<212> TYPE: DNA
<213> ORGANISM: Artificial Sequence
<220> FEATURE:
<223> OTHER INFORMATION: Illustrative nucleotide sequence.

<400> SEQUENCE: 2 cccgtgcat                                                              9

<210> SEQ ID NO 3
<211> LENGTH: 12
<212> TYPE: DNA
<213> ORGANISM: Artificial Sequence
<220> FEATURE:
<223> OTHER INFORMATION: Illustrative nucleotide sequence.

<400> SEQUENCE: 3
tcctgttgta tg                                                         12

<210> SEQ ID NO 4
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: (1)...(12)
```

```
<223> OTHER INFORMATION: n = A,T,C or G

<400> SEQUENCE: 4
ccannnnnnt gg                                                    12

<210> SEQ ID NO 5
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: (1)...(12)
<223> OTHER INFORMATION: n = A,T,C or G

<400> SEQUENCE: 5
ggtnnnnnna cc                                                    12

<210> SEQ ID NO 6
<211> LENGTH: 25
<212> TYPE: DNA
<213> ORGANISM: Artificial Sequence
<220> FEATURE:
<223> OTHER INFORMATION: Illustrative nucleotide sequence.

<400> SEQUENCE: 6
actgcaccgg aattctgtgc gtagg                                      25

<210> SEQ ID NO 7
<211> LENGTH: 25
<212> TYPE: DNA
<213> ORGANISM: Artificial Sequence
<220> FEATURE:
<223> OTHER INFORMATION: Illustrative nucleotide sequence.

<400> SEQUENCE: 7
tgacgtggcc ttaagacacg catcc                                      25

<210> SEQ ID NO 8
<211> LENGTH: 18
<212> TYPE: DNA
<213> ORGANISM: Artificial Sequence
<220> FEATURE:
<223> OTHER INFORMATION: Illustrative nucleotide sequence.

<400> SEQUENCE: 8
actaattctg tgcgtagg                                              18

<210> SEQ ID NO 9
<211> LENGTH: 17
<212> TYPE: DNA
<213> ORGANISM: Artificial Sequence
<220> FEATURE:
<223> OTHER INFORMATION: Illustrative nucleotide sequence.

<400> SEQUENCE: 9
tgacgtggcc ttaatcc                                               17
```